United States Patent [19]
Navab et al.

[11] Patent Number: 5,835,563
[45] Date of Patent: Nov. 10, 1998

[54] CALIBRATION APPARATUS FOR X-RAY GEOMETRY

[75] Inventors: Nassir Navab, Plainsboro; Ali Reza Bani-Hashemi, Belle Mead, both of N.J.

[73] Assignee: Siemens Corporate Research, Inc., Princeton, N.J.

[21] Appl. No.: 576,736

[22] Filed: Dec. 21, 1995

[51] Int. Cl.⁶ .................................................. G01D 18/00
[52] U.S. Cl. ........................ 378/207; 378/162; 378/163
[58] Field of Search .................................... 378/162, 163, 378/164, 165, 207

[56] References Cited

U.S. PATENT DOCUMENTS

| | | | |
|---|---|---|---|
| 3,952,194 | 4/1976 | Bayonnet | 378/163 X |
| 4,319,136 | 3/1982 | Jinkins | 250/456 |
| 4,341,220 | 7/1982 | Perry | 128/630 |
| 4,400,819 | 8/1983 | Bens et al. | 378/163 X |
| 4,838,265 | 6/1989 | Cosman et al. | 128/303 |
| 4,884,566 | 12/1989 | Mountz et al. | 378/163 X |
| 4,915,112 | 4/1990 | Singer | 378/163 X |
| 4,971,060 | 11/1990 | Schneider et al. | 378/163 X |
| 5,216,700 | 6/1993 | Cherian | 378/163 |
| 5,260,985 | 11/1993 | Mosby | 378/164 |

*Primary Examiner*—David P. Porta
*Attorney, Agent, or Firm*—Adel A. Ahmed

[57] ABSTRACT

Calibration apparatus for X-ray geometry, for use in conjunction with a portion of a patient's body to be X-rayed, an X-ray source, and imaging arrangement for forming an image, wherein the imaging arrangement is at a given orientation and distance from the portion of a patient's body, comprises a calibration ring adapted for being fastened to a portion of a patient's body, such as a patient's head. The ring exhibits a first degree of transparency to X-rays. An encoding arrangement incorporated in the ring comprises a plurality of encoding units exhibiting a second degree of transparency to X-rays, different from the first degree, the encoding units being arranged in a predetermined configuration such that an essentially two-dimensional projected image, formed by the imaging arrangement, of the calibration ring with the encoding arrangement exhibits a pattern of contrasting intensity attributable to at least a portion of the encoding arrangement from which the orientation and distance can be determined uniquely.

21 Claims, 8 Drawing Sheets

CALIBRATION APPARATUS FOR X-RAY GEOMETRY

The present application relates to apparatus for calibrating the geometry in an X-ray imaging configuration, and more particularly to apparatus wherein correlation can be established between a three dimensional object and a two-dimensional image.

There has been increasing interest in the reconstruction of vessel trees from X-ray angiograms, for which there are many applications. Various methods have been proposed and some such methods attempt to take into account the dynamics of the contrast bolus as it evolves over the Digital Subtraction Angiograph (DSA) sequence. These methods usually assume that the imaging system, that is the X-ray source and image intensifier system are rotating around a patient and are well calibrated. They therefore use the geometry of the imaging system for reconstruction of the vessel tree.

However, in practice many X-ray systems are not well calibrated, and the errors in calibration propagate through the reconstruction process and reduce the accuracy of the results.

Reference is hereby also made to a copending application in the name of the present inventors entitled CALIBRATION SYSTEM AND METHOD FOR X-RAY GEOMETRY and filed on even date with the present application. The said copending application is directed to closely related subject matter to the present application and the disclosure thereof, to the extent it is not inconsistent with the present application, is incorporated herein by reference.

Briefly, the said copending application discloses a system for X-ray geometry calibration comprises a calibration frame adapted for mounting proximate to at least a portion of a patient's body, such as a patient's head. An X-ray source cooperates with a target at a given orientation and distance from the portion of a patient's body for forming an image of the portion of a patient's body and of at least an associated portion of the calibration frame. The calibration frame includes encoding arrangement for uniquely determining correspondence between the image of the associated portion of the calibration frame and the calibration frame such that the orientation and distance can be determined uniquely from the image of the associated portion of the calibration frame.

Further disclosed in the said copending application is a system for X-ray geometry calibration comprises a calibration frame associated with a portion of a patient's body; an X-ray source; arrangement for forming an X-ray image of the portion of a patient's body and of the associated portion of the calibration frame; and wherein the calibration frame comprises encoding arrangement for determining a correspondence between the image of the associated portion of the calibration frame and the calibration frame for uniquely determining the correspondence uniquely from the image of the associated portion of the calibration frame.

Also disclosed in the said copending application is a method for determining correspondence between an X-ray image of a calibration frame associated with at least a portion of the body of a patient and the position of the calibration frame with respect to X-ray apparatus, comprises the steps of: (a) positioning an encoded three-dimensional calibration frame relative to at least a portion of a patient's body; (b) exposing the portion of a patient's body and at least a portion of the calibration frame to an X-ray source at a given orientation and distance therefrom so as to form a projected image of the portion of a patient's body and of the portion of the calibration frame; and (c) uniquely determining a correspondence between the image of the portion of the calibration frame and the three-dimensional calibration frame from observations of the image such that the orientation and distance are uniquely determined.

The said copending application further discloses a method for determining correspondence between an X-ray image of a calibration frame associated with at least a portion of the body of a patient and the position of the calibration frame with respect to X-ray apparatus, comprises the steps of: (a) positioning an encoded three-dimensional calibration frame relative to at least a portion of a patient's body, the calibration frame including therein an arrangement of spherules; (b) exposing the portion of a patient's body and at least a portion of the calibration frame to an X-ray source at a given orientation and distance therefrom so as to form a projected image of the portion of a patient's body and of the portion of the calibration frame; and (c) uniquely determining a correspondence between the image of the portion of the calibration frame and the three-dimensional calibration frame from observations of the image; and (d) computing the orientation and distance.

It is herein recognized that the algorithm in accordance with the present invention should provide for dynamic calibration of an X-ray system by introducing landmarks positioned around the patient within the region of interest. One object of the present invention is to achieve an intelligent design of such landmarks to obtain the most efficient and reliable calibration procedure.

In accordance with an aspect of the invention, calibration apparatus for X-ray geometry, for use in conjunction with a portion of a patient's body to be X-rayed, an X-ray source, and imaging arrangement for forming an image, wherein the imaging arrangement is at a given orientation and distance from the portion of a patient's body, comprises a calibration ring adapted for being fastened to a portion of a patient's body, the ring exhibiting a first degree of transparency to X-rays; and an encoding arrangement incorporated in the ring, comprising a plurality of encoding units exhibiting a second degree of transparency to X-rays, different from the first degree, the encoding units being arranged in a predetermined configuration such that an essentially two-dimensional projected image, formed by the imaging arrangement, of the calibration ring with the encoding arrangement exhibits a pattern of contrasting intensity attributable to at least a portion of the encoding arrangement from which the orientation and distance can be determined uniquely.

In accordance with another aspect of the invention, the predetermined configuration is in the form of a code of groups of units forming words and spaces therebetween in a sequence along the circumferential dimension of the calibration ring.

In accordance with still another aspect of the invention, none of the words occurs more than once in the predetermined configuration.

In accordance with yet another aspect of the invention, each word exhibits asymmetry such that it exhibits a different arrangement when read from one direction along the circumferential dimension to that which it exhibits when read along the opposite direction along the circumferential dimension.

In accordance with another aspect of the invention, each word does not form a valid word when read in the direction along the circumferential dimension opposite to the direction along the circumferential dimension in which it does form a valid word.

In accordance with yet another aspect of the invention, the ring is generally relatively transparent to X-rays and the encoding units comprise spherules relatively opaque to X-rays.

In accordance with yet another aspect of the invention, the ring is of a plastic material and spherules are metallic ball bearings.

In accordance with a further aspect of the invention, calibration apparatus for use in conjunction with X-ray imaging for establishing correspondence between a three-dimensional object and its two dimensional projection image, comprises a calibration ring associated with a portion of a the anatomy of a subject for X-ray examination, the ring comprising: a carrier portion adapted for attachment to the subject; encoding arrangement incorporated in the carrier portion of the calibration ring, the encoding arrangement comprising a plurality of code word configurations formed of a substance having a different degree of transparency from that of the carrier portion, the code word configurations being arranged in a sequence separated by spaces along a circumferential path along the ring in a given sense in which such words are to be read, such that no code word occurs more than once and no code word forms a valid word when read in a sense opposite the given sense.

In accordance with still a further aspect of the invention, the substance of which the code word configurations are formed is relatively opaque to X-rays and the carrier portion is made of a substance relatively transparent to X-rays.

In accordance with yet a further aspect of the invention, the code word configurations are formed of ball-bearing-like metallic balls.

In accordance with another aspect of the invention, calibration apparatus for use in conjunction with X-ray imaging for establishing correspondence between a three-dimensional object and its two dimensional projection image, comprises a calibration ring associated with a portion of a the anatomy of a subject for X-ray examination, the ring comprising: a carrier portion adapted for attachment to the subject; encoding arrangement incorporated in the carrier portion of the calibration ring, the encoding arrangement comprising a plurality of code word configurations formed of a substance for casting a calibration image in contrast to that of the carrier portion, such that the correspondence can be established uniquely from a portion, less than the whole, of the calibration image.

In accordance with an aspect of the invention, the calibration image provides unambiguous distinguishing information on the disposition of the calibration ring relative to the location of the calibration image.

In accordance with another aspect of the invention, the calibration image provides unambiguous distinguishing information on the disposition of the distal and proximate sides of the calibration ring relative to the location of the calibration image.

In accordance with yet another aspect of the invention, the calibration image provides unambiguous information on the location and orientation of the portion of the anatomy of a subject relative to a set of predetermined coordinates.

In accordance with an aspect of the invention, a calibration frame comprises a set of ball bearings positioned on a cylinder, herein referred to as a calibration ring. The structure of the calibration ring has been simulated. Different views of the calibration ring and, in particular, its image within a typical X-ray imaging system, are illustrated by using a simulation procedure in *Maple*.

The invention will be more fully understood from the detailed description of preferred embodiments which follows, in conjunction with the Drawing, in which.

Figure 1:
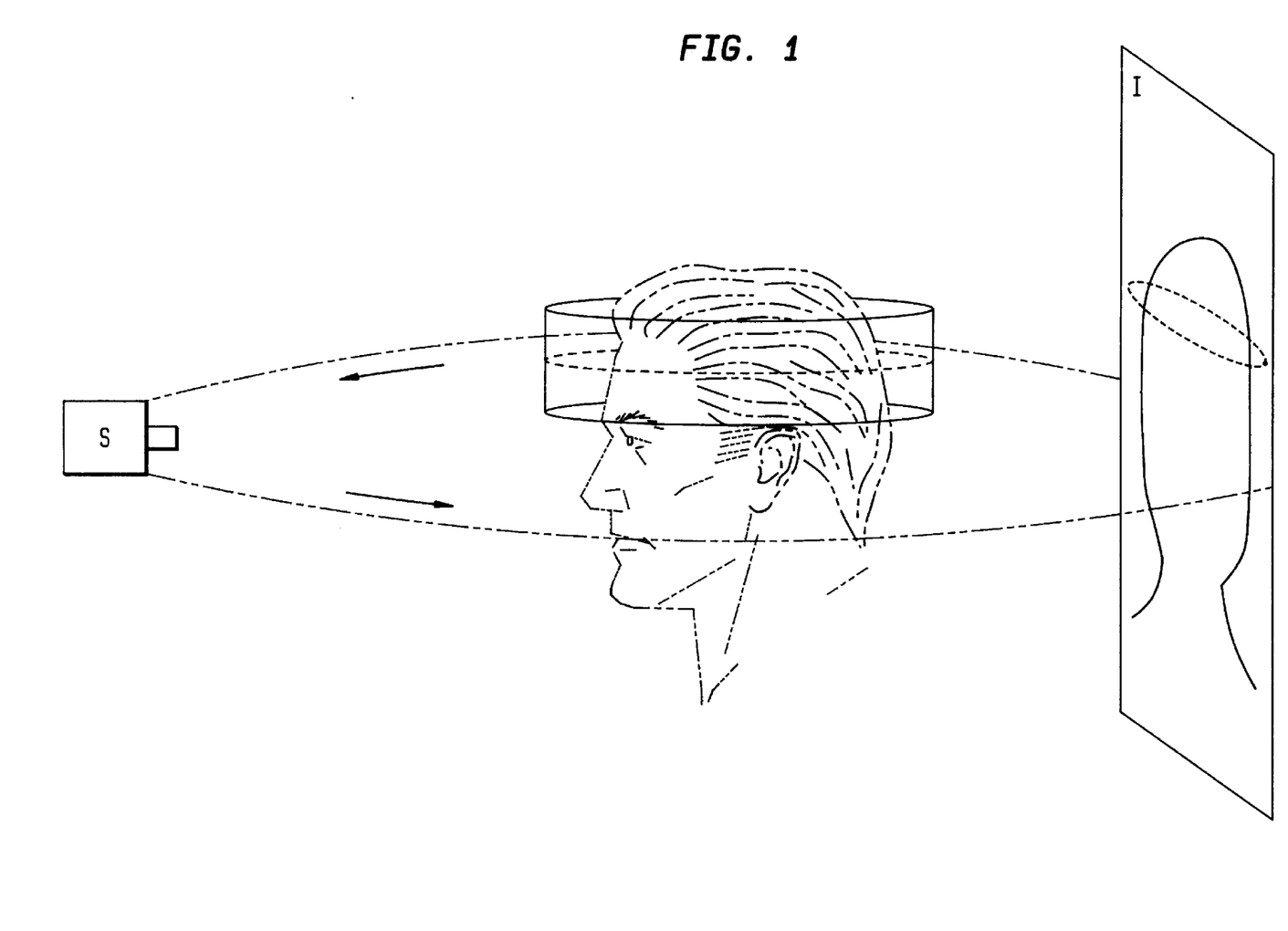
FIG. 1 shows a configuration for use in conjunction with the present invention showing the relative position of an X-ray source S, and image intensifier I, and a calibration frame F, in reference to a patient's head.
Figure 2A:
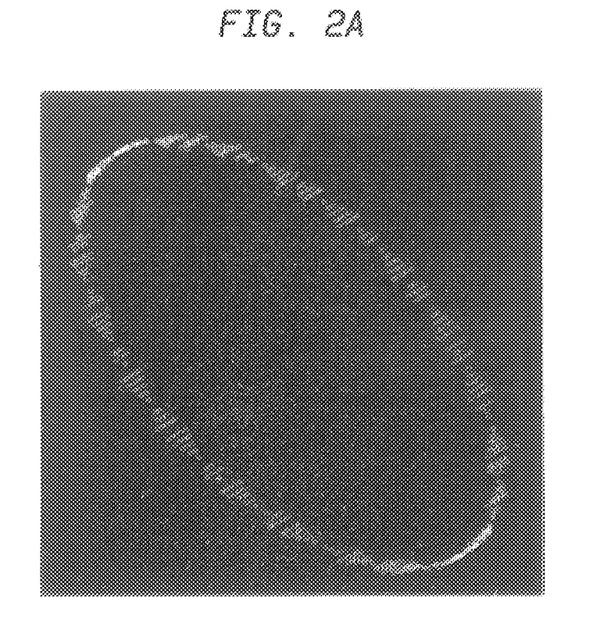
FIG. 2 shows a calibration ring in accordance with the present invention with perspective views (a) and (d), a top view (b), and a typical view in the application of the present invention (c)
Figure 2B:
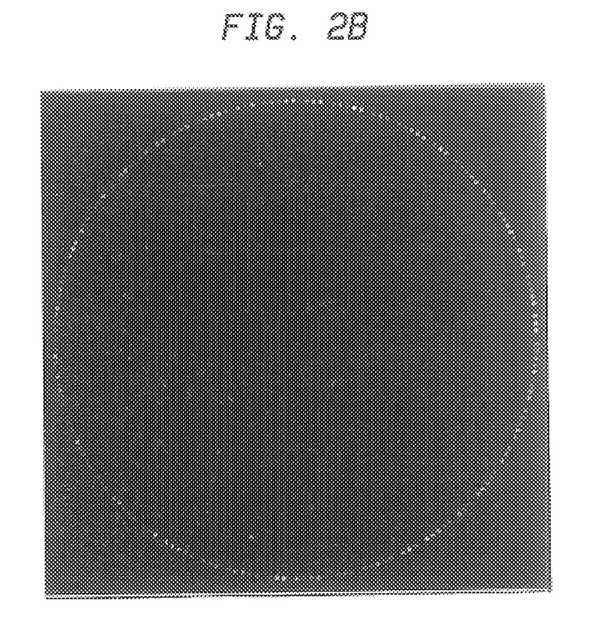
Figure 2C:
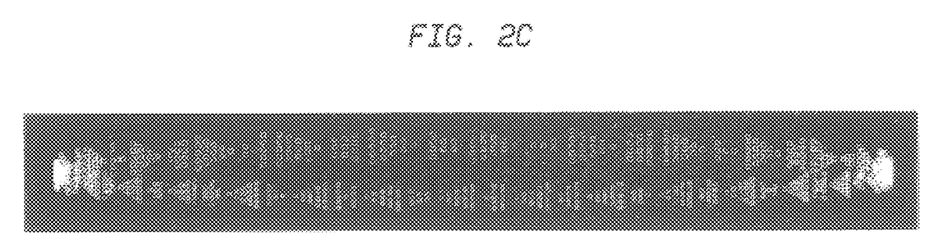
Figure 2D:
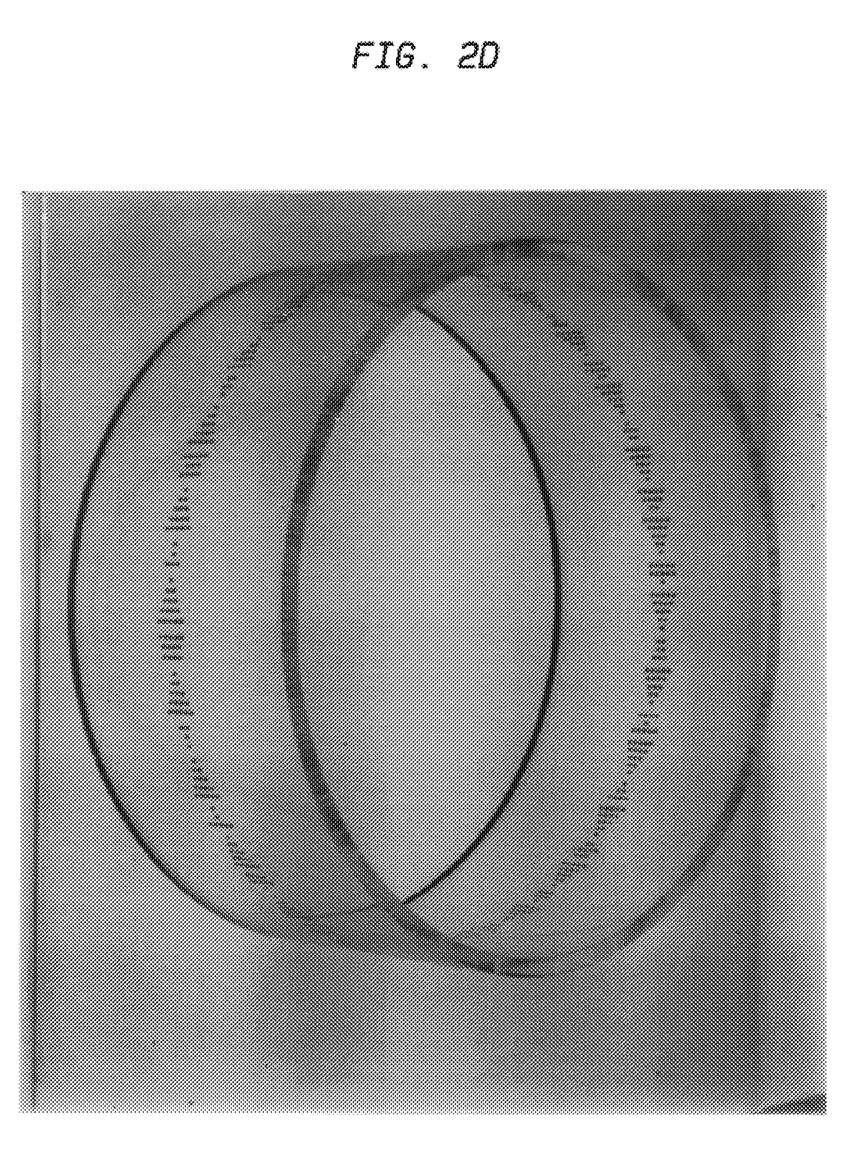
Figure 3:
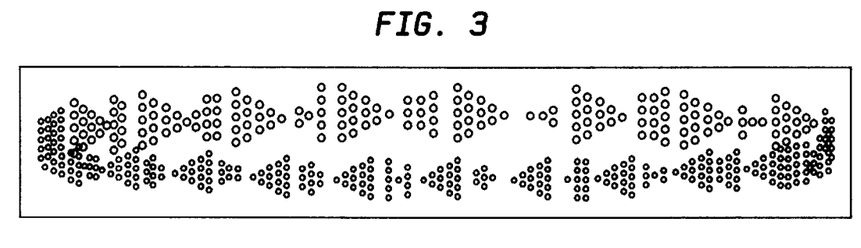
FIG. 3 shows a change in the size of spherules or ball bearings (BB's) and the spacing between them under a perspective projection, as applicable to an embodiment of the present invention.

The calibration apparatus in accordance with the invention are described in terms of an illustrative embodiment comprising a set of landmarks positioned around a patients head, the "calibration frame". FIG. 1 shows the relative position of an X-ray source S, an image intensifier I, the calibration frame F and a patient's head. A reference coordinate frame xyz is attached to the calibration frame. The three dimensional shape of the calibration frame is precisely known in this coordinate frame. The ball bearings incorporated in the calibration frame are made of steel which has a much higher absorption coefficient than human bones and tissue. This makes the detection and/or segmentation in the image much easier. It is noted that the procedures of detection, segmentation and calibration are known in the art and need not be further detailed herein.

A problem then is to first find the 3D-2D correspondence between the 3D model of the calibration frame and its image, and then to recover the position and orientation of the X-ray source in the reference coordinate frame xyz.

This problem is similar to what is called "recovery of absolute orientation" in photogrammetry, or "pose determination" in computer vision. It is an object of the invention that the 3D-2D correspondences can be easily and unambiguously determined. The calibration ring is utilized for the reconstruction of a small region of interest (local reconstruction). The image acquisition setup is such that the region of interest will fill the entire field of view, meaning that only a portion of the calibration ring will be present in the X-ray image. It is herein recognized that the design of the calibration ring must be smart enough so one can unambiguously determine the part of the ring that appears in the image.

The calibration frame in accordance with the present invention comprises a circular ring $R_0$ formed by a set of ball bearings (BBs). The calibration ring will be described in further detail subsequently. FIG. 2 shows a top view and a perspective view of the calibration frame in accordance with the invention. It will explained further below why this is a smart disposition of calibration BBs. The calibration procedure comprises the following steps: detecting the projections of spheres (BBs) on the X-ray images based on the variation of X-ray image intensity; find the 2D-3D correspondences between image and the calibration ring; compute the orientation of the camera R and its location T in the coordinate system associated with the calibration ring.

The design of the calibration ring is important with regard to the invention since it affects all three steps of the method. Accordingly, a design is next introduced. The present inventors have performed simulation of the structure of the calibration ring in order to illustrate performance. Different views of the calibration ring and in particular its image within a typical X-ray imaging system are shown by way of simulation procedures using the software Maple.

It is herein recognized that the calibration ring should be designed such that 3D-2D correspondence can be easily and unambiguously determined. In addition to determining such correspondence from one view only, it is desirable to find the correspondence from a partial view of the calibration frame in the event it may be necessary to focus on some particular part of, for example, a patient's brain. In accordance with the described exemplary embodiment, the calibration frame comprises a circular ring $R_0$ formed by a set of ball bearings (BBs). Subsets of BBs are arranged vertically around the circumference of the ring $R_0$. Sequences of such arrangements define code words in order to encode different sections of the ring. In designing this coding, the following considerations apply. The relative spacing between BBs will vary under perspective projection. Therefore, the spacing between BBs is not utilized for encoding the calibration frame.

However, the spacing for facilitating this decoding process can be utilized, as will be explained further in due course. The sizes of BBs will vary under perspective projection. Accordingly, the different sizes of BBs are not utilized for encoding the calibration frame. Thus, one may choose two BBs, one quite small and the other relatively large to make sure that, under typical perspective transformation they remain distinguishable. In this case the detection of small BBs may become quite difficult and imprecise because of their reduced size. To solve this problem, a material of high X-ray absorption coefficient may be utilized; however, this may lead in turn to image saturation for large BBs, which makes the detection of their centroid difficult and imprecise. Therefore, the same size BBs are utilized in the construction of the ring.

In accordance with an embodiment of the invention, a particular arrangement of BBs is used to define a spacing word (Blank Space) between two consecutive codes. To define the Blank Space and other code words on the Ring, the following rules are followed. No word other than Blank Space occurs more than once. In X-ray imaging, surface patches will image differently depending upon the sign of the surface normal component in the viewing direction. Therefore, a word may be projected in two different ways, one being a flipped version of the other, depending on the relative positioning of the ring and imaging system.

Figure 4:
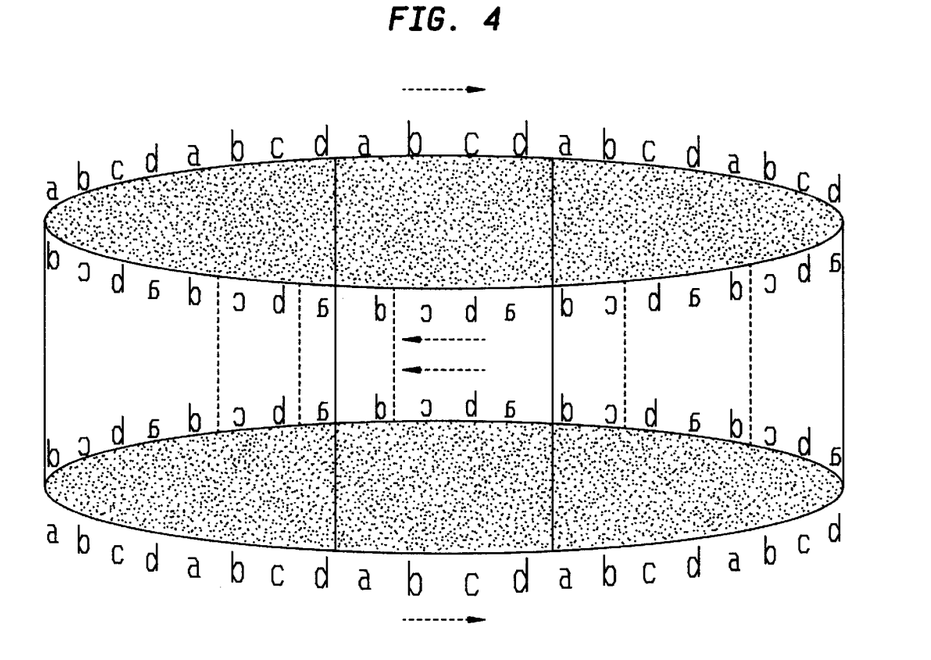
FIG. 4 shows a view of a cylinder, applicable to the present invention, wherein the center of projection is out of the cylinder between its two bases, indicating that words incorporated therein are flipped when the sign of the surface normal component in the viewing direction changes.
Figure 5:
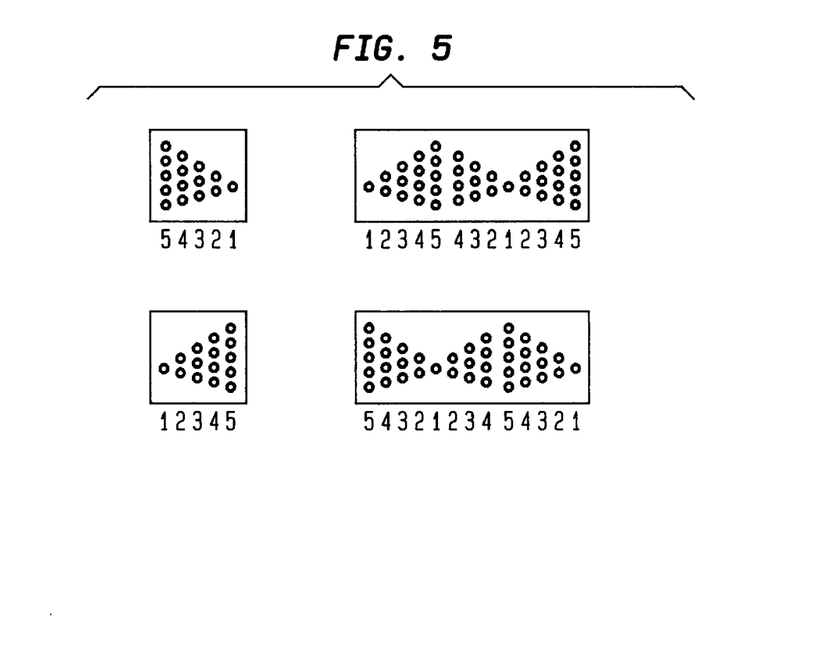
FIG. 5, applicable to an embodiment of the present invention, shows how a Blank Space is the five digit code 54321 or 12345 depending on the sign of the surface normal component in the viewing direction (a), and how this arrangement is excluded to disambiguate detection of Blank Space (b)

FIG. 4 gives a clear example of this effect. A transparent cylinder is viewed. The center of projection is out of the cylinder between its two bases. It can be noted how the words are flipped when the sign of the surface normal component in the viewing direction changes. A further rule is that a word cannot be a code word if its flipped version is a codeword. In particular, no symmetric word can be a code word. In the exemplary embodiment, the Blank Space is the five-digit code 54321 or 12345 depending on the sign of the surface normal component in the viewing direction (see FIGS. 5 and 6). The positioning codes are 3 digit words in base 6. The word 234 (or 432) is excluded to disambiguate detection of Blank Space (see FIG. ). W is the set of all possible code words when following all the rules and remarks described earlier:

W = [ 112, 445, 311, 435, 122, 255, 114, 543, 321, 524, 213, 452, 132, 542, 551, 223, 415, 124, 253, 331, 235, 241, 145, 412, 154, 511, 244, 215, 334, 422, 225, 143, 513, 134, 531, 152, 441, 233, 342, 521, 423, 314, 351]

Figure 6:
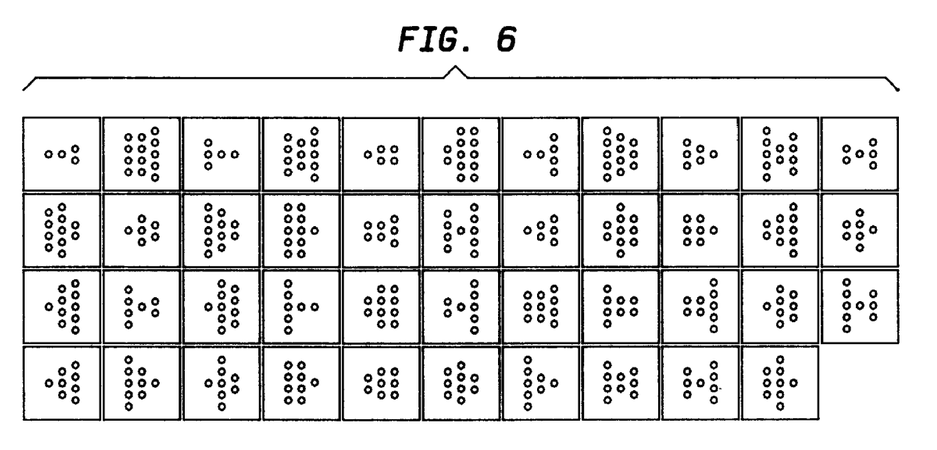
FIG. 6 shows a table of consecutive words for an embodiment of the present invention which table is sorted such that the total number of BB's in consecutive words varies as little as possible.

FIG. 6 shows a picture of W: The total number of visible BBs in partial views (see FIG. 9) of the ring should vary as little as possible. This helps keeping a uniform precision in the calibration result. The code words in W are sorted such that the total number of BBs in consecutive words varies as little as possible. This means that a code with a small number of BBs, e.g. the code 112, with only 4 BBs, is followed by a code with a large number of BBs, e.g. 112 is followed by 445. Accordingly it is preferable to use an even number of code words. Therefore, in the exemplary embodiment, the distance between consecutive BBs is modified, if necessary, in order to have an even number of code words. Blank Space has 5 digits and 15 BBs (FIG. 5) while a code word has only 3 digits and an average of 8 BBs. In a small window containing one word and one Blank Space, this leads to a small ratio between variation in number of visible BBs ±5 over their average number 23.

If the Blank Space had less digits or BBs, this ratio would undesirably increase. The design of the calibration ring may go through different changes during the testing process. Therefore, the present invention incorporates flexible design, where the radius of the ring R, radius of BBs r, the spacing between codewords $d_2$, and horizontal/vertical BBs inter-distances within a code word, respectively $d_1$ and $d_3$, are all variables. In addition to the foregoing description of the geometry of an exemplary implementation of the calibration ring, there is described in the following the designing algorithm, with an example to give different measurements.

Figure 7:
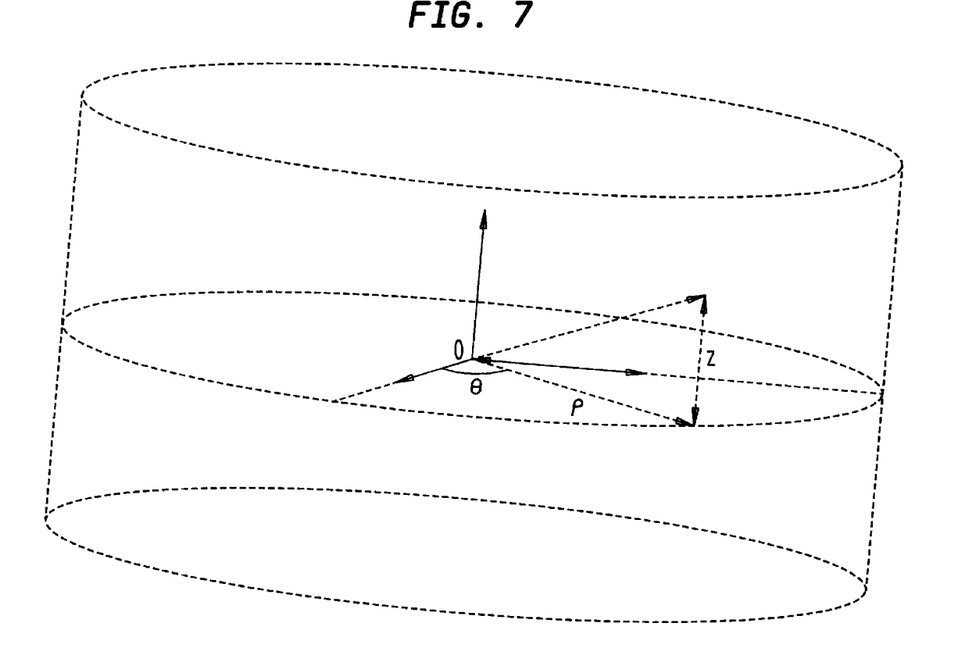
FIG. 7 shows a cylindrical coordinate system as applied to an embodiment of the present invention, wherein the center of the coordinate system is at the center of the cylindrical support and each point is defined by its three coordinates $\Theta$, $\rho$, and z.

This information is contemplated to be helpful in the design of additional embodiments for new rings as may be required, by simply varying some of the parameters. The design results in a particular arrangement of BBs. Therefore, it gives a set of BBs positions in a particular coordinate system attached to the ring. A cylindrical coordinate system is preferred as an apparently natural choice. The center of the coordinate system is taken to be at the center of the cylindrical support of the calibration ring. Each point, being the position of a BB, is defined by its three coordinates $\Theta$, $\rho$, z in FIG. 7.

Since all BBs are positioned on the ring, $\rho=R$ for all points. All the parameters in the design, $\Theta$, $\alpha_1$, $\alpha_2$, $d_1$, $d_2$, and $d_3$ are functions of the size of the calibration ring and that of the BBs (R and r). In the present exemplary embodiment, BBs of radius r=0.6 mm are utilized, and the BBs are located on a cylinder of radius R=114.54 mm. The tube used is cast acrylic, with an average outside diameter of 224.7 mm. BBs are placed on a band of a Lexan sheet of 1.58 mm thickness which is then rolled to outer circumference of the tube. It is apparent from this how the parameters of the calibration ring are defined and at each step, an example is given using the values obtained for the exemplary implementation.

Figure 8:
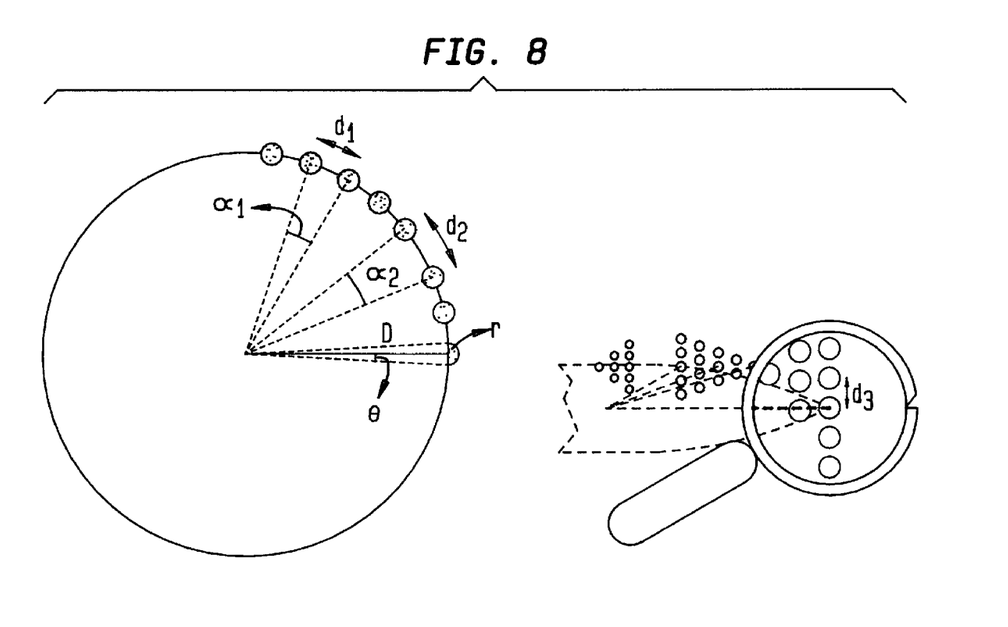
FIG. 8 shows parameters of a calibration ring in accordance with an embodiment of the present invention, in a top view (a) and in a side view (b)

First, $\Theta$ is defined (FIG. 8):

$$\theta = \arcsin\left(\frac{r}{R}\right)$$

For example, $$\theta = \text{Arctan}\left(\frac{0.6}{112.37}\right) = 0.0053 \text{ radians}$$

$\alpha_1$ in FIG. 8 defines the angle between centers of two consecutive BBs on the ring in radians. If these BBs are in touch, this angle equals $2*\Theta$. To facilitate detection there should be provided a spacing between BBs. The bigger are the BBs, the larger the spacing should be. Accordingly, the spacing is defined to have an angular distance of $\lambda_1*\Theta$ around the ring between BBs. In a first implementation, $\lambda_1=3$.

Therefore, $\alpha_1=2\Theta+\lambda_1\Theta$;

For example, $\alpha_1=0.026$ radians.

Therefore the arclength between centers of two consecutive BBs in a code word in millimeters is $d_1=\alpha_1 R$;

For example, $d_1=2.98$ mm

In the same way, the distance between two consecutive code words can be defined. It is desirable to make this distance also a function of BB's size, $\lambda_2*\Theta$ but more than the distance between consecutive BBs inside the code.

In a first implementation, $\lambda_2=5.5$. The angle and the arclength between center of the last BB of a code word to the center of the first BB of the next code (see FIG. 8), respectively in radians and millimeters, are:

$\alpha_2=2\Theta+\lambda_2\Theta$; for example, $\alpha_2=0.0397$ radians $d_2=\alpha_2 R$; for example, $d_2=4.46$ mm.

The ring comprises a series of consecutive pairs of Blank Space and code words. If Blank Space and codewords are respectively of M and N digits, M=5 and N=3 in the first implementation, then the angle occupied by each consecutive pair around the calibration ring is:

$s=(N+M-2)\alpha_1+2\alpha_2$; For example, $s=0.238$ radians.

The maximum number of (Blank+code) words that can be positioned around the ring is then:

$$k = \text{trunc}\left(\frac{2\pi}{s}\right);$$

for example, k=26

Next, $\alpha_2$ now has to be adjusted so as to ensure a regular spacing between words. Note that if k (Blank+code) are used as defined above, then there is an extra space of $2\pi-ks$ between the last code and the first space. In the present example, this spacing is $2\pi-26*0.238=6.283-6.188=0.095$ radians. This extra space around the ring is therefore equally distributed to all spaces between consecutive code words:

$$\alpha 2 = \alpha 2 + \left(\frac{\pi}{k} - \frac{s}{2}\right);$$

for example, $\alpha_2=0.0414$ radians
and therefore $d_2$ is also modified:
$d_2=\alpha_2 R$;
for example, $d_2=4.65$ mm The last parameter to set is the vertical distance between BBs, $d_3$ in FIG. 8. If the two BBs touch each other then $d_3=2r$. This distance should also be a function of the BB's radius $d_3=2*r+\lambda_3*r$. In addition, $\lambda_3$ should be chosen such that a vertically arranged group of BBs, defining one digit of a code word, would be easily separated from the neighboring other digits. This means that a condition should be imposed that $\lambda_3<\lambda_1<\lambda_2$.

In the first implementation, $\lambda_3$ is taken as lambda $\lambda_3=1$ and $d_3=4.2r=2.5$ mm.

Now the ring can be built up. The second cylindrical coordinates of all points on the ring are the same $\rho=R$. The two other parameters, $\Theta$ and z define the position of each BB on the ring. The procedure begins at the point of coordinates ($\Theta=0$, $\rho=R$, z=0), or simply (0,R,0). It then places appropriately all words and blank space around the ring. It indeed alternates a Blank Space and a word W[i], i=1 . . ,s, from the coding table of the coding table of FIG. 6.

Unless BBs are too small or the ring is too large, W will always provide enough code words (more than s—s=26 in the first implementation). A final verification is made that an even number of code words is utilized and if not, $\lambda_1$ and $\lambda_2$ are modified and, in consequence $l_1$ and $l_2$ to have an even number of code words around the Calibration Ring.

Figure 9A:
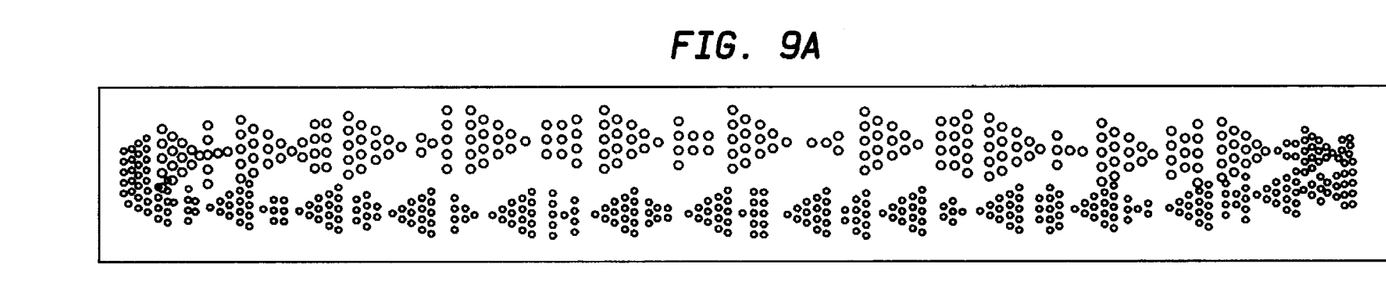
FIG. 9 shows simulation results for an X-ray image of a calibration ring in a typical X-ray imaging system in accordance with the present invention, in a complete view (a) and in a partial view (b) which is the more typical image in a local reconstruction application for the present invention.
Figure 9B:
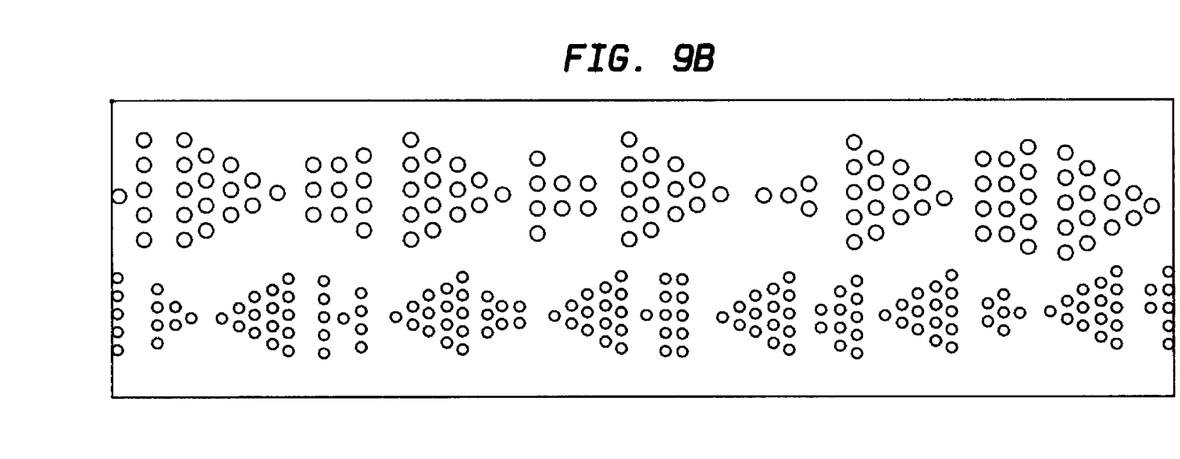

613 BBs are used in the first design. The tables following in the Appendix give the position of all 613 BBs. A complete simulation of the calibration ring and the imaging geometry has been built, using Maple. FIG. 9 simulates the image obtainable with a typical X-ray imaging geometry. In this simulation, the distance between the X-ray source and the image intensifier is 98 cm, the ring is centered 78 cm away from X-ray source, and the image size is taken to be 17 $cm^2$.

Clearly, the present invention can be implemented in conjunction with the use of a suitably programmed digital computer, using programming techniques known in the art.

The invention has been described by way of exemplary embodiments. It will nevertheless be understood by those of skill in the art to which it pertains that various changes and modifications can be made without departing from the teaching and spirit of the invention. For example, it will be apparent that various encoding schemes are possible as variants of those herein described. Furthermore, it will be apparent that an inversion whereby opaque and transparent portions are interchanged is feasible without any significant alteration of the operation. Such changes and the like are intended to be within the scope of the invention, which is defined by the claims following.

APPENDIX

| k | x | y | z |
|---|---|---|---|
| 1 | 112.37 | 0 | -5.0006 |
| 2 | 112.37 | 0 | -2.5003 |
| 3 | 112.37 | 0 | 0 |
| 4 | 112.37 | 0 | 2.5003 |
| 5 | 112.37 | 0 | 5.0006 |
| 6 | 112.33 | 2.9762 | -3.7505 |
| 7 | 112.33 | 2.9762 | -1.2502 |
| 8 | 112.33 | 2.9762 | 1.2502 |

APPENDIX-continued

| k | x | y | z |
|---|---|---|---|
| 9 | 112.33 | 2.9762 | 3.7505 |
| 10 | 112.21 | 5.9504 | −2.5003 |
| 11 | 112.21 | 5.9504 | 0 |
| 12 | 112.21 | 5.9504 | 2.5003 |
| 13 | 112.01 | 8.9203 | −1.2502 |
| 14 | 112.01 | 8.9203 | 1.2502 |
| 15 | 111.74 | 11.884 | 0 |
| 16 | 111.15 | 16.494 | 0 |
| 17 | 110.67 | 19.432 | 0 |
| 18 | 110.12 | 22.357 | −1.2502 |
| 19 | 110.12 | 22.357 | 1.2502 |
| 20 | 109.1 | 26.891 | −5.0006 |
| 21 | 109.1 | 26.891 | −2.5003 |
| 22 | 109.1 | 26.891 | 0 |
| 23 | 109.1 | 26.891 | 2.5003 |
| 24 | 109.1 | 26.891 | 5.0006 |
| 25 | 108.35 | 29.772 | −3.7505 |
| 26 | 108.35 | 29.772 | −1.2502 |
| 27 | 108.35 | 29.772 | 1.2502 |
| 28 | 108.35 | 29.772 | 3.7505 |
| 29 | 107.53 | 32.631 | −2.5003 |
| 30 | 107.53 | 32.631 | 0 |
| 31 | 107.53 | 32.631 | 2.5003 |
| 32 | 106.62 | 35.468 | −1.2502 |
| 33 | 106.62 | 35.468 | 1.2502 |
| 34 | 105.65 | 38.279 | 0 |
| 35 | 103.97 | 42.615 | −3.7505 |
| 36 | 103.97 | 42.615 | −1.2502 |
| 37 | 103.97 | 42.615 | 1.2502 |
| 38 | 103.97 | 42.615 | 3.7505 |
| 39 | 102.81 | 45.354 | −3.7505 |
| 40 | 102.81 | 45.354 | −1.2502 |
| 41 | 102.81 | 45.354 | 1.2502 |
| 42 | 102.81 | 45.354 | 3.7505 |
| 43 | 101.57 | 48.061 | −5.0006 |
| 44 | 101.57 | 48.061 | −2.5003 |
| 45 | 101.57 | 48.061 | 0 |
| 46 | 101.57 | 48.061 | 2.5003 |
| 47 | 101.57 | 48.061 | 5.0006 |
| 48 | 99.497 | 52.22 | −5.0006 |
| 49 | 99.497 | 52.22 | −2.5003 |
| 50 | 99.497 | 52.22 | 0 |
| 51 | 99.497 | 52.22 | 2.5003 |
| 52 | 99.497 | 52.22 | 5.0006 |
| 53 | 98.079 | 54.837 | −3.7505 |
| 54 | 98.079 | 54.837 | −1.2502 |
| 55 | 98.079 | 54.837 | 1.2502 |
| 56 | 98.079 | 54.837 | 3.7505 |
| 57 | 96.592 | 57.416 | −2.5003 |
| 58 | 96.592 | 57.416 | 0 |
| 59 | 96.592 | 57.416 | 2.5003 |
| 60 | 95.037 | 59.954 | −1.2502 |
| 61 | 95.037 | 59.954 | 1.2502 |
| 62 | 93.416 | 62.45 | 0 |
| 63 | 90.754 | 66.259 | −2.5003 |
| 64 | 90.754 | 66.259 | 0 |
| 65 | 90.754 | 66.259 | 2.5003 |
| 66 | 88.967 | 68.64 | 0 |
| 67 | 87.118 | 70.972 | 0 |
| 68 | 84.109 | 74.514 | −5.0006 |
| 69 | 84.109 | 74.514 | −2.5003 |
| 70 | 84.109 | 74.514 | 0 |
| 71 | 84.109 | 74.514 | 2.5003 |
| 72 | 84.109 | 74.514 | 5.0006 |
| 73 | 82.106 | 76.715 | −3.7505 |
| 74 | 82.106 | 76.715 | −1.2502 |
| 75 | 82.106 | 76.715 | 1.2502 |
| 76 | 82.106 | 76.715 | 3.7505 |
| 77 | 80.045 | 78.863 | −2.5003 |
| 78 | 80.045 | 78.863 | 0 |
| 79 | 80.045 | 78.863 | 2.5003 |
| 80 | 77.928 | 80.956 | −1.2502 |
| 81 | 77.928 | 80.956 | 1.2502 |
| 82 | 75.756 | 82.991 | 0 |
| 83 | 72.26 | 86.053 | −3.7505 |
| 84 | 72.26 | 86.053 | −1.2502 |
| 85 | 72.26 | 86.053 | 1.2502 |
| 86 | 72.26 | 86.053 | 3.7505 |
| 87 | 69.955 | 87.936 | −2.5003 |
| 88 | 69.955 | 87.936 | 0 |
| 89 | 69.955 | 87.936 | 2.5003 |
| 90 | 67.602 | 89.758 | −5.0006 |
| 91 | 67.602 | 89.758 | −2.5003 |
| 92 | 67.602 | 89.758 | 0 |
| 93 | 67.602 | 89.758 | 2.5003 |
| 94 | 67.602 | 89.758 | 5.0006 |
| 95 | 63.832 | 92.477 | −5.0006 |
| 96 | 63.832 | 92.477 | −2.5003 |
| 97 | 63.832 | 92.477 | 0 |
| 98 | 63.832 | 92.477 | 2.5003 |
| 99 | 63.832 | 92.477 | 5.0006 |
| 100 | 61.361 | 94.135 | −3.7505 |
| 101 | 61.361 | 94.135 | −1.2502 |
| 102 | 61.361 | 94.135 | 1.2502 |
| 103 | 61.361 | 94.135 | 3.7505 |
| 104 | 58.846 | 95.728 | −2.5003 |
| 105 | 58.846 | 95.728 | 0 |
| 106 | 58.846 | 95.728 | 2.5003 |
| 107 | 56.29 | 97.253 | −1.2502 |
| 108 | 56.29 | 97.253 | 1.2502 |
| 109 | 53.694 | 98.709 | 0 |
| 110 | 49.566 | 100.85 | 0 |
| 111 | 46.878 | 102.12 | −1.2502 |
| 112 | 46.878 | 102.12 | 1.2502 |
| 113 | 44.157 | 103.33 | −1.2502 |
| 114 | 44.157 | 103.33 | 1.2502 |
| 115 | 39.846 | 105.07 | −5.0006 |
| 116 | 39.846 | 105.07 | −2.5003 |
| 117 | 39.846 | 105.07 | 0 |
| 118 | 39.846 | 105.07 | 2.5003 |
| 119 | 39.846 | 105.07 | 5.0006 |
| 120 | 37.049 | 106.08 | −3.7505 |
| 121 | 37.049 | 106.08 | −1.2502 |
| 122 | 37.049 | 106.08 | 1.2502 |
| 123 | 37.049 | 106.08 | 3.7505 |
| 124 | 34.227 | 107.03 | −2.5003 |
| 125 | 34.227 | 107.03 | 0 |
| 126 | 34.227 | 107.03 | 2.5003 |
| 127 | 31.38 | 107.9 | −1.2502 |
| 128 | 31.38 | 107.9 | 1.2502 |
| 129 | 28.511 | 108.69 | 0 |
| 130 | 23.992 | 109.78 | −1.2502 |
| 131 | 23.992 | 109.78 | 1.2502 |
| 132 | 21.076 | 110.37 | −5.0006 |
| 133 | 21.076 | 110.37 | −2.5003 |
| 134 | 21.076 | 110.37 | 0 |
| 135 | 21.076 | 110.37 | 2.5003 |
| 136 | 21.076 | 110.37 | 5.0006 |
| 137 | 18.145 | 110.89 | −5.0006 |
| 138 | 18.145 | 110.89 | −2.5003 |
| 139 | 18.145 | 110.89 | 0 |
| 140 | 18.145 | 110.89 | 2.5003 |
| 141 | 18.145 | 110.89 | 5.0006 |
| 142 | 13.544 | 111.55 | −5.0006 |
| 143 | 13.544 | 111.55 | −2.5003 |
| 144 | 13.544 | 111.55 | 0 |
| 145 | 13.544 | 111.55 | 2.5003 |
| 146 | 13.544 | 111.55 | 5.0006 |
| 147 | 10.585 | 111.87 | −3.7505 |
| 148 | 10.585 | 111.87 | −1.2502 |
| 149 | 10.585 | 111.87 | 1.2502 |
| 150 | 10.585 | 111.87 | 3.7505 |
| 151 | 7.6185 | 112.11 | −2.5003 |
| 152 | 7.6185 | 112.11 | 0 |
| 153 | 7.6185 | 112.11 | 2.5003 |
| 154 | 4.6464 | 112.27 | −1.2502 |
| 155 | 4.6464 | 112.27 | 1.2502 |
| 156 | 1.6711 | 112.36 | 0 |
| 157 | −2.9762 | 112.33 | 0 |
| 158 | −5.9504 | 112.21 | 0 |
| 159 | −8.9203 | 112.01 | −3.7505 |
| 160 | −8.9203 | 112.01 | −1.2502 |
| 161 | −8.9203 | 112.01 | 1.2502 |
| 162 | −8.9203 | 112.01 | 3.7505 |

APPENDIX-continued

| k | x | y | z |
|---|---|---|---|
| 163 | −13.544 | 111.55 | −5.0006 |
| 164 | −13.544 | 111.55 | −2.5003 |
| 165 | −13.544 | 111.55 | 0 |
| 166 | −13.544 | 111.55 | 2.5003 |
| 167 | −13.544 | 111.55 | 5.0006 |
| 168 | −16.494 | 111.15 | −3.7505 |
| 169 | −16.494 | 111.15 | −1.2502 |
| 170 | −16.494 | 111.15 | 1.2502 |
| 171 | −16.494 | 111.15 | 3.7505 |
| 172 | −19.432 | 110.67 | −2.5003 |
| 173 | −19.432 | 110.67 | 0 |
| 174 | −19.432 | 110.67 | 2.5003 |
| 175 | −22.357 | 110.12 | −1.2502 |
| 176 | −22.357 | 110.12 | 1.2502 |
| 177 | −25.266 | 109.49 | 0 |
| 178 | −29.772 | 108.35 | −5.0006 |
| 179 | −29.772 | 108.35 | −2.5003 |
| 180 | −29.772 | 108.35 | 0 |
| 181 | −29.772 | 108.35 | 2.5003 |
| 182 | −29.772 | 108.35 | 5.0006 |
| 183 | −32.631 | 107.53 | −3.7505 |
| 184 | −32.631 | 107.53 | −1.2502 |
| 185 | −32.631 | 107.53 | 1.2502 |
| 186 | −32.631 | 107.53 | 3.7505 |
| 187 | −35.468 | 106.62 | −2.5003 |
| 188 | −35.468 | 106.62 | 0 |
| 189 | −35.468 | 106.62 | 2.5003 |
| 190 | −39.846 | 105.07 | −5.0006 |
| 191 | −39.846 | 105.07 | −2.5003 |
| 192 | −39.846 | 105.07 | 0 |
| 193 | −39.846 | 105.07 | 2.5003 |
| 194 | −39.846 | 105.07 | 5.0006 |
| 195 | −42.615 | 103.97 | −3.7505 |
| 196 | −42.615 | 103.97 | −1.2502 |
| 197 | −42.615 | 103.97 | 1.2502 |
| 198 | −42.615 | 103.97 | 3.7505 |
| 199 | −45.354 | 102.81 | −2.5003 |
| 200 | −45.354 | 102.81 | 0 |
| 201 | −45.354 | 102.81 | 2.5003 |
| 202 | −48.061 | 101.57 | −1.2502 |
| 203 | −48.061 | 101.57 | 1.2502 |
| 204 | −50.735 | 100.26 | 0 |
| 205 | −54.837 | 98.079 | −2.5003 |
| 206 | −54.837 | 98.079 | 0 |
| 207 | −54.837 | 98.079 | 2.5003 |
| 208 | −57.416 | 96.592 | −1.2502 |
| 209 | −57.416 | 96.592 | 1.2502 |
| 210 | −59.954 | 95.037 | 0 |
| 211 | −63.832 | 92.477 | −5.0006 |
| 212 | −63.832 | 92.477 | −2.5003 |
| 213 | −63.832 | 92.477 | 0 |
| 214 | −63.832 | 92.477 | 2.5003 |
| 215 | −63.832 | 92.477 | 5.0006 |
| 216 | −66.259 | 90.754 | −3.7505 |
| 217 | −66.259 | 90.754 | −1.2502 |
| 218 | −66.259 | 90.754 | 1.2502 |
| 219 | −66.259 | 90.754 | 3.7505 |
| 220 | −68.64 | 88.967 | −2.5003 |
| 221 | −68.64 | 88.967 | 0 |
| 222 | −68.64 | 88.967 | 2.5003 |
| 223 | −70.972 | 87.118 | −1.2502 |
| 224 | −70.972 | 87.118 | 1.2502 |
| 225 | −73.255 | 85.208 | 0 |
| 226 | −76.715 | 82.106 | −5.0006 |
| 227 | −76.715 | 82.106 | −2.5003 |
| 228 | −76.715 | 82.106 | 0 |
| 229 | −76.715 | 82.106 | 2.5003 |
| 230 | −76.715 | 82.106 | 5.0006 |
| 231 | −78.863 | 80.045 | −1.2502 |
| 232 | −78.863 | 80.045 | 1.2502 |
| 233 | −80.956 | 77.928 | −3.7505 |
| 234 | −80.956 | 77.928 | −1.2502 |
| 235 | −80.956 | 77.928 | 1.2502 |
| 236 | −80.956 | 77.928 | 3.7505 |
| 237 | −84.109 | 74.514 | −5.0006 |
| 238 | −84.109 | 74.514 | −2.5003 |
| 239 | −84.109 | 74.514 | 0 |
| 240 | −84.109 | 74.514 | 2.5003 |
| 241 | −84.109 | 74.514 | 5.0006 |
| 242 | −86.053 | 72.26 | −3.7505 |
| 243 | −86.053 | 72.26 | −1.2502 |
| 244 | −86.053 | 72.26 | 1.2502 |
| 245 | −86.053 | 72.26 | 3.7505 |
| 246 | −87.936 | 69.955 | −2.5003 |
| 247 | −87.936 | 69.955 | 0 |
| 248 | −87.936 | 69.955 | 2.5003 |
| 249 | −89.758 | 67.602 | −1.2502 |
| 250 | −89.758 | 67.602 | 1.2502 |
| 251 | −91.518 | 65.201 | 0 |
| 252 | −94.135 | 61.361 | −1.2502 |
| 253 | −94.135 | 61.361 | 1.2502 |
| 254 | −95.728 | 58.846 | 0 |
| 255 | −97.253 | 56.29 | −2.5003 |
| 256 | −97.253 | 56.29 | 0 |
| 257 | −97.253 | 56.29 | 2.5003 |
| 258 | −99.497 | 52.22 | −5.0006 |
| 259 | −99.497 | 52.22 | −2.5003 |
| 260 | −99.497 | 52.22 | 0 |
| 261 | −99.497 | 52.22 | 2.5003 |
| 262 | −99.497 | 52.22 | 5.0006 |
| 263 | −100.85 | 49.566 | −3.7505 |
| 264 | −100.85 | 49.566 | −1.2502 |
| 265 | −100.85 | 49.566 | 1.2502 |
| 266 | −100.85 | 49.566 | 3.7505 |
| 267 | −102.12 | 46.878 | −2.5003 |
| 268 | −102.12 | 46.878 | 0 |
| 269 | −102.12 | 46.878 | 2.5003 |
| 270 | −103.33 | 44.157 | −1.2502 |
| 271 | −103.33 | 44.157 | 1.2502 |
| 272 | −104.46 | 41.404 | 0 |
| 273 | −106.08 | 37.049 | −3.7505 |
| 274 | −106.08 | 37.049 | −1.2502 |
| 275 | −106.08 | 37.049 | 1.2502 |
| 276 | −106.08 | 37.049 | 3.7505 |
| 277 | −107.03 | 34.227 | −5.0006 |
| 278 | −107.03 | 34.227 | −2.5003 |
| 279 | −107.03 | 34.227 | 0 |
| 280 | −107.03 | 34.227 | 2.5003 |
| 281 | −107.03 | 34.227 | 5.0006 |
| 282 | −107.9 | 31.38 | −1.2502 |
| 283 | −107.9 | 31.38 | 1.2502 |
| 284 | −109.1 | 26.891 | −5.0006 |
| 285 | −109.1 | 26.891 | −2.5003 |
| 286 | −109.1 | 26.891 | 0 |
| 287 | −109.1 | 26.891 | 2.5003 |
| 288 | −109.1 | 26.891 | 5.0006 |
| 289 | −109.78 | 23.992 | −3.7505 |
| 290 | −109.78 | 23.992 | −1.2502 |
| 291 | −109.78 | 23.992 | 1.2502 |
| 292 | −109.78 | 23.992 | 3.7505 |
| 293 | −110.37 | 21.076 | −2.5003 |
| 294 | −110.37 | 21.076 | 0 |
| 295 | −110.37 | 21.076 | 2.5003 |
| 296 | −110.89 | 18.145 | −1.2502 |
| 297 | −110.89 | 18.145 | 1.2502 |
| 298 | −111.33 | 15.202 | 0 |
| 299 | −111.87 | 10.585 | 0 |
| 300 | −112.11 | 7.6185 | −2.5003 |
| 301 | −112.11 | 7.6185 | 0 |
| 302 | −112.11 | 7.6185 | 2.5003 |
| 303 | −112.27 | 4.6464 | −1.2502 |
| 304 | −112.27 | 4.6464 | 1.2502 |
| 305 | −112.37 | 0.00000000000000015312 | −5.0006 |
| 306 | −112.37 | 0.00000000000000015312 | −2.5003 |
| 307 | −112.37 | 0.00000000000000015312 | 0 |
| 308 | −112.37 | 0.00000000000000015312 | 2.5003 |
| 309 | −112.37 | 0.00000000000000015312 | 5.0006 |
| 310 | −112.33 | −2.9762 | −3.7505 |
| 311 | −112.33 | −2.9762 | −1.2502 |
| 312 | −112.33 | −2.9762 | 1.2502 |
| 313 | −112.33 | −2.9762 | 3.7505 |
| 314 | −112.21 | −5.9504 | −2.5003 |
| 315 | −112.21 | −5.9504 | 0 |
| 316 | −112.21 | −5.9504 | 2.5003 |

APPENDIX-continued

| k | x | y | z |
|---|---|---|---|
| 317 | −112.01 | −8.9203 | −1.2502 |
| 318 | −112.01 | −8.9203 | 1.2502 |
| 319 | −111.74 | −11.884 | 0 |
| 320 | −111.15 | −16.494 | −5.0006 |
| 321 | −111.15 | −16.494 | −2.5003 |
| 322 | −111.15 | −16.494 | 0 |
| 323 | −111.15 | −16.494 | 2.5003 |
| 324 | −111.15 | −16.494 | 5.0006 |
| 325 | −110.67 | −19.432 | −3.7505 |
| 326 | −110.67 | −19.432 | −1.2502 |
| 327 | −110.67 | −19.432 | 1.2502 |
| 328 | −110.67 | −19.432 | 3.7505 |
| 329 | −110.12 | −22.357 | −1.2502 |
| 330 | −110.12 | −22.357 | 1.2502 |
| 331 | −109.1 | −26.891 | −5.0006 |
| 332 | −109.1 | −26.891 | −2.5003 |
| 333 | −109.1 | −26.891 | 0 |
| 334 | −109.1 | −26.891 | 2.5003 |
| 335 | −109.1 | −26.891 | 5.0006 |
| 336 | −108.35 | −29.772 | −3.7505 |
| 337 | −108.35 | −29.772 | −1.2502 |
| 338 | −108.35 | −29.772 | 1.2502 |
| 339 | −108.35 | −29.772 | 3.7505 |
| 340 | −107.53 | −32.631 | −2.5003 |
| 341 | −107.53 | −32.631 | 0 |
| 342 | −107.53 | −32.631 | 2.5003 |
| 343 | −106.62 | −35.468 | −1.2502 |
| 344 | −106.62 | −35.468 | 1.2502 |
| 345 | −105.65 | −38.279 | 0 |
| 346 | −103.97 | −42.615 | −5.0006 |
| 347 | −103.97 | −42.615 | −2.5003 |
| 348 | −103.97 | −42.615 | 0 |
| 349 | −103.97 | −42.615 | 2.5003 |
| 350 | −103.97 | −42.615 | 5.0006 |
| 351 | −102.81 | −45.354 | −5.0006 |
| 352 | −102.81 | −45.354 | −2.5003 |
| 353 | −102.81 | −45.354 | 0 |
| 354 | −102.81 | −45.354 | 2.5003 |
| 355 | −102.81 | −45.354 | 5.0006 |
| 356 | −101.57 | −48.061 | 0 |
| 357 | −99.497 | −52.22 | −5.0006 |
| 358 | −99.497 | −52.22 | −2.5003 |
| 359 | −99.497 | −52.22 | 0 |
| 360 | −99.497 | −52.22 | 2.5003 |
| 361 | −99.497 | −52.22 | 5.0006 |
| 362 | −98.079 | −54.837 | −3.7505 |
| 363 | −98.079 | −54.837 | −1.2502 |
| 364 | −98.079 | −54.837 | 1.2502 |
| 365 | −98.079 | −54.837 | 3.7505 |
| 366 | −96.592 | −57.416 | −2.5003 |
| 367 | −96.592 | −57.416 | 0 |
| 368 | −96.592 | −57.416 | 2.5003 |
| 369 | −95.037 | −59.954 | −1.2502 |
| 370 | −95.037 | −59.954 | 1.2502 |
| 371 | −93.416 | −62.45 | 0 |
| 372 | −90.754 | −66.259 | −1.2502 |
| 373 | −90.754 | −66.259 | 1.2502 |
| 374 | −88.967 | −68.64 | −1.2502 |
| 375 | −88.967 | −68.64 | 1.2502 |
| 376 | −87.118 | −70.972 | −2.5003 |
| 377 | −87.118 | −70.972 | 0 |
| 378 | −87.118 | −70.972 | 2.5003 |
| 379 | −84.109 | −74.514 | −5.0006 |
| 380 | −84.109 | −74.514 | −2.5003 |
| 381 | −84.109 | −74.514 | 0 |
| 382 | −84.109 | −74.514 | 2.5003 |
| 383 | −84.109 | −74.514 | 5.0006 |
| 384 | −82.106 | −76.715 | −3.7505 |
| 385 | −82.106 | −76.715 | −1.2502 |
| 386 | −82.106 | −76.715 | 1.2502 |
| 387 | −82.106 | −76.715 | 3.7505 |
| 388 | −80.045 | −78.863 | −2.5003 |
| 389 | −80.045 | −78.863 | 0 |
| 390 | −80.045 | −78.863 | 2.5003 |
| 391 | −77.928 | −80.956 | −1.2502 |
| 392 | −77.928 | −80.956 | 1.2502 |
| 393 | −75.756 | −82.991 | 0 |
| 394 | −72.26 | −86.053 | −3.7505 |
| 395 | −72.26 | −86.053 | −1.2502 |
| 396 | −72.26 | −86.053 | 1.2502 |
| 397 | −72.26 | −86.053 | 3.7505 |
| 398 | −69.955 | −87.936 | 0 |
| 399 | −67.602 | −89.758 | −5.0006 |
| 400 | −67.602 | −89.758 | −2.5003 |
| 401 | −67.602 | −89.758 | 0 |
| 402 | −67.602 | −89.758 | 2.5003 |
| 403 | −67.602 | −89.758 | 5.0006 |
| 404 | −63.832 | −92.477 | −5.0006 |
| 405 | −63.832 | −92.477 | −2.5003 |
| 406 | −63.832 | −92.477 | 0 |
| 407 | −63.832 | −92.477 | 2.5003 |
| 408 | −63.832 | −92.477 | 5.0006 |
| 409 | −61.361 | −94.135 | −3.7505 |
| 410 | −61.361 | −94.135 | −1.2502 |
| 411 | −61.361 | −94.135 | 1.2502 |
| 412 | −61.361 | −94.135 | 3.7505 |
| 413 | −58.846 | −95.728 | −2.5003 |
| 414 | −58.846 | −95.728 | 0 |
| 415 | −58.846 | −95.728 | 2.5003 |
| 416 | −56.29 | −97.253 | −1.2502 |
| 417 | −56.29 | −97.253 | 1.2502 |
| 418 | −53.694 | −98.709 | 0 |
| 419 | −49.566 | −100.85 | 0 |
| 420 | −46.878 | −102.12 | −1.2502 |
| 421 | −46.878 | −102.12 | 1.2502 |
| 422 | −44.157 | −103.33 | −3.7505 |
| 423 | −44.157 | −103.33 | −1.2502 |
| 424 | −44.157 | −103.33 | 1.2502 |
| 425 | −44.157 | −103.33 | 3.7505 |
| 426 | −39.846 | −105.07 | −5.0006 |
| 427 | −39.846 | −105.07 | −2.5003 |
| 428 | −39.846 | −105.07 | 0 |
| 429 | −39.846 | −105.07 | 2.5003 |
| 430 | −39.846 | −105.07 | 5.0006 |
| 431 | −37.049 | −106.08 | −3.7505 |
| 432 | −37.049 | −106.08 | −1.2502 |
| 433 | −37.049 | −106.08 | 1.2502 |
| 434 | −37.049 | −106.08 | 3.7505 |
| 435 | −34.227 | −107.03 | −2.5003 |
| 436 | −34.227 | −107.03 | 0 |
| 437 | −34.227 | −107.03 | 2.5003 |
| 438 | −31.38 | −107.9 | −1.2502 |
| 439 | −31.38 | −107.9 | 1.2502 |
| 440 | −28.511 | −108.69 | 0 |
| 441 | −23.992 | −109.78 | −1.2502 |
| 442 | −23.992 | −109.78 | 1.2502 |
| 443 | −21.076 | −110.37 | −5.0006 |
| 444 | −21.076 | −110.37 | −2.5003 |
| 445 | −21.076 | −110.37 | 0 |
| 446 | −21.076 | −110.37 | 2.5003 |
| 447 | −21.076 | −110.37 | 5.0006 |
| 448 | −18.145 | −110.89 | −2.5003 |
| 449 | −18.145 | −110.89 | 0 |
| 450 | −18.145 | −110.89 | 2.5003 |
| 451 | −13.544 | −111.55 | −5.0006 |
| 452 | −13.544 | −111.55 | −2.5003 |
| 453 | −13.544 | −111.55 | 0 |
| 454 | −13.544 | −111.55 | 2.5003 |
| 455 | −13.544 | −111.55 | 5.0006 |
| 456 | −10.585 | −111.87 | −3.7505 |
| 457 | −10.585 | −111.87 | −1.2502 |
| 458 | −10.585 | −111.87 | 1.2502 |
| 459 | −10.585 | −111.87 | 3.7505 |
| 460 | −7.6185 | −112.11 | −2.5003 |
| 461 | −7.6185 | −112.11 | 0 |
| 462 | −7.6185 | −112.11 | 2.5003 |
| 463 | −4.6464 | −112.27 | −1.2502 |
| 464 | −4.6464 | −112.27 | 1.2502 |
| 465 | −1.6711 | −112.36 | 0 |
| 466 | 2.9762 | −112.33 | −2.5003 |
| 467 | 2.9762 | −112.33 | 0 |
| 468 | 2.9762 | −112.33 | 2.5003 |
| 469 | 5.9504 | −112.21 | −2.5003 |
| 470 | 5.9504 | −112.21 | 0 |

APPENDIX-continued

| k | x | y | z |
|---|---|---|---|
| 471 | 5.9504 | −112.21 | 2.5003 |
| 472 | 8.9203 | −112.01 | 0 |
| 473 | 13.544 | −111.55 | −5.0006 |
| 474 | 13.544 | −111.55 | −2.5003 |
| 475 | 13.544 | −111.55 | 0 |
| 476 | 13.544 | −111.55 | 2.5003 |
| 477 | 13.544 | −111.55 | 5.0006 |
| 478 | 16.494 | −111.15 | −3.7505 |
| 479 | 16.494 | −111.15 | −1.2502 |
| 480 | 16.494 | −111.15 | 1.2502 |
| 481 | 16.494 | −111.15 | 3.7505 |
| 482 | 19.432 | −110.67 | −2.5003 |
| 483 | 19.432 | −110.67 | 0 |
| 484 | 19.432 | −110.67 | 2.5003 |
| 485 | 22.357 | −110.12 | −1.2502 |
| 486 | 22.357 | −110.12 | 1.2502 |
| 487 | 25.266 | −109.49 | 0 |
| 488 | 29.772 | −108.35 | −1.2502 |
| 489 | 29.772 | −108.35 | 1.2502 |
| 490 | 32.631 | −107.53 | −2.5003 |
| 491 | 32.631 | −107.53 | 0 |
| 492 | 32.631 | −107.53 | 2.5003 |
| 493 | 35.468 | −106.62 | −5.0006 |
| 494 | 35.468 | −106.62 | −2.5003 |
| 495 | 35.468 | −106.62 | 0 |
| 496 | 35.468 | −106.62 | 2.5003 |
| 497 | 35.468 | −106.62 | 5.0006 |
| 498 | 39.846 | −105.07 | −5.0006 |
| 499 | 39.846 | −105.07 | −2.5003 |
| 500 | 39.846 | −105.07 | 0 |
| 501 | 39.846 | −105.07 | 2.5003 |
| 502 | 39.846 | −105.07 | 5.0006 |
| 503 | 42.615 | −103.97 | −3.7505 |
| 504 | 42.615 | −103.97 | −1.2502 |
| 505 | 42.615 | −103.97 | 1.2502 |
| 506 | 42.615 | −103.97 | 3.7505 |
| 507 | 45.354 | −102.81 | −2.5003 |
| 508 | 45.354 | −102.81 | 0 |
| 509 | 45.354 | −102.81 | 2.5003 |
| 510 | 48.061 | −101.57 | −1.2502 |
| 511 | 48.061 | −101.57 | 1.2502 |
| 512 | 50.735 | −100.26 | 0 |
| 513 | 54.837 | −98.079 | −1.2502 |
| 514 | 54.837 | −98.079 | 1.2502 |
| 515 | 57.416 | −96.592 | −3.7505 |
| 516 | 57.416 | −96.592 | −1.2502 |
| 517 | 57.416 | −96.592 | 1.2502 |
| 518 | 57.416 | −96.592 | 3.7505 |
| 519 | 59.954 | −95.037 | 0 |
| 520 | 63.832 | −92.477 | −5.0006 |
| 521 | 63.832 | −92.477 | −2.5003 |
| 522 | 63.832 | −92.477 | 0 |
| 523 | 63.832 | −92.477 | 2.5003 |
| 524 | 63.832 | −92.477 | 5.0006 |
| 525 | 66.259 | −90.754 | −3.7505 |
| 526 | 66.259 | −90.754 | −1.2502 |
| 527 | 66.259 | −90.754 | 1.2502 |
| 528 | 66.259 | −90.754 | 3.7505 |
| 529 | 68.64 | −88.967 | −2.5003 |
| 530 | 68.64 | −88.967 | 0 |
| 531 | 68.64 | −88.967 | 2.5003 |
| 532 | 70.972 | −87.118 | −1.2502 |
| 533 | 70.972 | −87.118 | 1.2502 |
| 534 | 73.255 | −85.208 | 0 |
| 535 | 76.715 | −82.106 | 0 |
| 536 | 78.863 | −80.045 | −3.7505 |
| 537 | 78.863 | −80.045 | −1.2502 |
| 538 | 78.863 | −80.045 | 1.2502 |
| 539 | 78.863 | −80.045 | 3.7505 |
| 540 | 80.956 | −77.928 | −5.0006 |
| 541 | 80.956 | −77.928 | −2.5003 |
| 542 | 80.956 | −77.928 | 0 |
| 543 | 80.956 | −77.928 | 2.5003 |
| 544 | 80.956 | −77.928 | 5.0006 |
| 545 | 84.109 | −74.514 | −5.0006 |
| 546 | 84.109 | −74.514 | −2.5003 |
| 547 | 84.109 | −74.514 | 0 |
| 548 | 84.109 | −74.514 | 2.5003 |
| 549 | 84.109 | −74.514 | 5.0006 |
| 550 | 86.053 | −72.26 | −3.7505 |
| 551 | 86.053 | −72.26 | −1.2502 |
| 552 | 86.053 | −72.26 | 1.2502 |
| 553 | 86.053 | −72.26 | 3.7505 |
| 554 | 87.936 | −69.955 | −2.5003 |
| 555 | 87.936 | −69.955 | 0 |
| 556 | 87.936 | −69.955 | 2.5003 |
| 557 | 89.758 | −67.602 | −1.2502 |
| 558 | 89.758 | −67.602 | 1.2502 |
| 559 | 91.518 | −65.201 | 0 |
| 560 | 94.135 | −61.361 | −3.7505 |
| 561 | 94.135 | −61.361 | −1.2502 |
| 562 | 94.135 | −61.361 | 1.2502 |
| 563 | 94.135 | −61.361 | 3.7505 |
| 564 | 95.728 | −58.846 | 0 |
| 565 | 97.253 | −56.29 | −1.2502 |
| 566 | 97.253 | −56.29 | 1.2502 |
| 567 | 99.497 | −52.22 | −5.0006 |
| 568 | 99.497 | −52.22 | −2.5003 |
| 569 | 99.497 | −52.22 | 0 |
| 570 | 99.497 | −52.22 | 2.5003 |
| 571 | 99.497 | −52.22 | 5.0006 |
| 572 | 100.85 | −49.566 | −3.7505 |
| 573 | 100.85 | −49.566 | −1.2502 |
| 574 | 100.85 | −49.566 | 1.2502 |
| 575 | 100.85 | −49.566 | 3.7505 |
| 576 | 102.12 | −46.878 | −2.5003 |
| 577 | 102.12 | −46.878 | 0 |
| 578 | 102.12 | −46.878 | 2.5003 |
| 579 | 103.33 | −44.157 | −1.2502 |
| 580 | 103.33 | −44.157 | 1.2502 |
| 581 | 104.46 | −41.404 | 0 |
| 582 | 106.08 | −37.049 | 0 |
| 583 | 107.03 | −34.227 | −5.0006 |
| 584 | 107.03 | −34.227 | −2.5003 |
| 585 | 107.03 | −34.227 | 0 |
| 586 | 107.03 | −34.227 | 2.5003 |
| 587 | 107.03 | −34.227 | 5.0006 |
| 588 | 107.9 | −31.38 | −3.7505 |
| 589 | 107.9 | −31.38 | −1.2502 |
| 590 | 107.9 | −31.38 | 1.2502 |
| 591 | 107.9 | −31.38 | 3.7505 |
| 592 | 109.1 | −26.891 | −5.0006 |
| 593 | 109.1 | −26.891 | −2.5003 |
| 594 | 109.1 | −26.891 | 0 |
| 595 | 109.1 | −26.891 | 2.5003 |
| 596 | 109.1 | −26.891 | 5.0006 |
| 597 | 109.78 | −23.992 | −3.7505 |
| 598 | 109.78 | −23.992 | −1.2502 |
| 599 | 109.78 | −23.992 | 1.2502 |
| 600 | 109.78 | −23.992 | 3.7505 |
| 601 | 110.37 | −21.076 | −2.5003 |
| 602 | 110.37 | −21.076 | 0 |
| 603 | 110.37 | −21.076 | 2.5003 |
| 604 | 110.89 | −18.145 | −1.2502 |
| 605 | 110.89 | −18.145 | 1.2502 |
| 606 | 111.33 | −15.202 | 0 |
| 607 | 111.87 | −10.585 | −5.0006 |
| 608 | 111.87 | −10.585 | −2.5003 |
| 609 | 111.87 | −10.585 | 0 |
| 610 | 111.87 | −10.585 | 2.5003 |
| 611 | 111.87 | −10.585 | 5.0006 |
| 612 | 112.11 | −7.6185 | 0 |
| 613 | 112.27 | −4.6464 | 0 |

What is claimed is:

1. Calibration apparatus for X-ray geometry, for use in conjunction with a portion of a patient's body to be X-rayed, an X-ray source, and imaging means for forming an image, wherein said imaging means is at a given orientation and distance from said portion of a patient's body, said apparatus comprising:

a calibration ring adapted for being fastened to a portion of a patient's body, said ring exhibiting a first degree of transparency to X-rays and being positioned such that one side of said calibration ring is proximate said X-ray source and the opposite side is distal thereto; and encoding means incorporated in said ring, comprising a plurality of encoding units exhibiting a second degree of transparency to X-rays, different from said first degree, said encoding units being arranged in a predetermined configuration such that an essentially two-dimensional projected image, formed by said imaging means, of said calibration ring with said encoding means exhibits a pattern of contrasting intensity attributable to at least a portion of said encoding means incorporated in said proximate side of said calibration ring and at least a portion of said encoding means incorporated in said distal side, from which said orientation and distance can be determined uniquely.

2. Calibration apparatus in accordance with claim 1, wherein said predetermined configuration is in the form of a code of groups of units forming words and spaces therebetween in a sequence along the circumferential dimension of said calibration ring.

3. Calibration apparatus in accordance with claim 2, wherein none of said words occurs more than once in said predetermined configuration.

4. Calibration apparatus in accordance with claim 3, wherein each word exhibits asymmetry such that it exhibits a different arrangement when read from one direction along said circumferential dimension to that which it exhibits when read along the opposite direction along said circumferential dimension.

5. Calibration apparatus in accordance with claim 3, wherein each word does not form a valid word when read in the direction along said circumferential dimension opposite to the direction along said circumferential dimension in which it does form a valid word.

6. Calibration apparatus in accordance with claim 1, wherein said ring is generally relatively transparent to X-rays and said encoding units comprise spherules relatively opaque to X-rays.

7. Calibration apparatus in accordance with claim 6, wherein said ring is of a plastic material and spherules are metallic ball bearings.

8. Calibration apparatus for use in conjunction with X-ray imaging for establishing correspondence between a three-dimensional object and its two dimensional projection image, said apparatus comprising a calibration ring associated with a portion of a the anatomy of a subject for X-ray examination by positioning said ring between an X-ray source and an imaging plane disposed on opposite sides thereof for forming a two-dimensional image including at least a portion of each of said opposite sides, said ring comprising:

a carrier portion adapted for attachment to said subject;

encoding means incorporated in said carrier portion of said calibration ring, said encoding means comprising a plurality of code word configurations formed of a substance having a different degree of transparency from that of said carrier portion, said code word configurations being arranged in a sequence separated by spaces along a circumferential path along said ring in a given sense in which such words are to be read, such that no code word occurs more than once and no code word forms a valid word when read in a sense opposite said given sense.

9. Calibration apparatus in accordance with claim 8, wherein said substance of which said code word configurations are formed is relatively opaque to X-rays and said carrier portion is made of a substance relatively transparent to X-rays.

10. Calibration apparatus in accordance with claim 9, wherein said code word configurations are formed of ball-bearing-like metallic balls.

11. Calibration apparatus for use in conjunction with X-ray imaging for establishing correspondence between a three-dimensional object and its two dimensional projection image, said apparatus comprising a calibration ring associated with a portion of a the anatomy of a subject for X-ray examination by positioning said ring between an X-ray source and an imaging plane disposed on opposite sides thereof for forming a two-dimensional image including at least a portion of each of said opposite sides, said ring comprising:

a carrier portion adapted for attachment to said subject;

encoding means incorporated in said carrier portion of said calibration ring, said encoding means comprising a plurality of code word configurations formed of a substance for casting a calibration image inset two dimensional in contrast to that of said carrier portion, such that said correspondence can be established uniquely from a portion, less than the whole, of said calibration image.

12. Calibration apparatus in accordance with claim 11, wherein said calibration image provides unambiguous distinguishing information on the disposition of said calibration ring relative to the location of said calibration image.

13. Calibration apparatus in accordance with claim 11, wherein said calibration image provides unambiguous distinguishing information on the disposition of the distal and proximate sides of said calibration ring relative to the location of said calibration image.

14. Calibration apparatus in accordance with claim 13, wherein said calibration image provides unambiguous information on the location and orientation of said portion of the anatomy of a subject relative to a set of predetermined coordinates.

15. Calibration apparatus for X-ray geometry, for use in conjunction with a portion of a patient's body to be X-rayed, an X-ray source, and imaging means for forming an image, wherein said imaging means is at a given orientation and distance from said portion of a patient's body, said apparatus comprising:

a calibration ring adapted for being fastened to a portion of a patient's body, said ring exhibiting a first degree of transparency to X-rays; and encoding means incorporated in said ring, comprising a plurality of encoding units exhibiting a second degree of transparency to X-rays, different from said first degree, said encoding units being arranged in a predetermined configuration such that an essentially two-dimensional projected image, formed by said imaging means, of said calibration ring with said encoding means exhibits a pattern of contrasting intensity attributable to at least a portion of said encoding means from which said orientation and distance can be determined uniquely, wherein said predetermined configuration is in the form of a code of groups of units forming words and spaces therebetween in a sequence along the circumferential dimension of said calibration ring.

16. Calibration apparatus in accordance with claim 15, wherein none of said words occurs more than once in said predetermined configuration.

17. Calibration apparatus in accordance with claim 16, wherein each word exhibits asymmetry such that it exhibits a different arrangement when read from one direction along said circumferential dimension to that which it exhibits when read along the opposite direction along said circumferential dimension.

18. Calibration apparatus in accordance with claim 16, wherein each word does not form a valid word when read in the direction along said circumferential dimension opposite to the direction along said circumferential dimension in which it does form a valid word.

19. Calibration apparatus in accordance with claim 15, wherein said ring is generally relatively transparent to x-rays and said encoding units comprise spherules relatively opaque to x-rays.

20. Calibration apparatus in accordance with claim 19, wherein said ring is of a plastic material and spherules are metallic ball bearings.

21. Calibration apparatus for use in conjunction with X-ray imaging for establishing correspondence between a three-dimensional object and its two dimensional projection image, said apparatus comprising a calibration ring associated with a portion of a the anatomy of a subject for X-ray examination, said ring comprising:

a carrier portion adapted for attachment to said subject;

encoding means incorporated in said carrier portion of said calibration ring, said encoding means comprising a plurality of code word configurations formed of a substance having a different degree of transparency from that of said carrier portion, said code word configurations being arranged in a sequence separated by spaces along a circumferential path along said ring in a given sense in which such words are to be read, such that no code word occurs more than once and no code word forms a valid word when read in a sense opposite said given sense, said substance of which said code word configurations are formed being relatively opaque to X-rays, said carrier portion being made of a substance relatively transparent to X-rays, and said code word configurations being formed of ball-bearing-like metallic balls.

* * * * *